US00PP32234P3

(12) United States Plant Patent
Fouillet

(10) Patent No.: US PP32,234 P3
(45) Date of Patent: Sep. 29, 2020

(54) APPLE TREE NAMED 'Y103'

(50) Latin Name: *Malus domestica*
Varietal Denomination: Y103

(71) Applicant: IFO S.A.R.L.

(72) Inventor: Valérie Fouillet, Saint Sylvain d'Anjou (FR)

(73) Assignee: IFO S.A.R.L., Seiches sur le Loir ( * ) Notice: Subject to any disclaimer, the term of this patent is extended or adjusted under 35 U.S.C. 154(b) by 58 days.

(21) Appl. No.: 16/350,339

(22) Filed: Oct. 31, 2018

(65) Prior Publication Data

US 2020/0137937 P1 Apr. 30, 2020

(30) Foreign Application Priority Data

Nov. 20, 2017 (FR) ..... PBR 20789

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
See application file for complete search history.

(56) References Cited

PUBLICATIONS

UPOV PLUTO: Plant Variety Database, citation for 'Y103' (1 page).*

* cited by examiner

*Primary Examiner* — Susan McCormick Ewoldt
(74) *Attorney, Agent, or Firm* — Michelle Bos Legal LLC

(57) ABSTRACT

'Y103' apple tree is a new variety selected for its distinctive dark pink and white fleshed fruit, which is well-suited for the fresh market.

6 Drawing Sheets

Latin name: *Malus domestica.*
Variety denomination: 'Y103'.

BACKGROUND OF THE VARIETY

'Y103' is a new and distinct variety of apple tree (*Malus domestica*) obtained from a controlled cross of 'Golden Delicious' (female parent, not patented) x 'SJ109' (male parent, not patented) carried out at Seiches sur le Loir, France in 2006. Seeds obtained from the cross were planted at Seiches sur le Loir, and 'Y103' was selected from the resulting seedlings for propagation and further observation. 'Y103' was first asexually propagated by grafting in 2011 at Seiches sur le Loir, and has since been observed to remain true to type over successive asexually propagated generations.

BRIEF DESCRIPTION OF THE VARIETY

'Y103' apple tree is distinguished by its fruit, which has dark pink red and white flesh and is well-suited for fresh consumption. 'Y103' is distinguished from its parents and related variety 'Y101' (U.S. Plant Pat. No. 28,201) as shown in the tables below.

TABLE 1

Comparison of 'Y103' to 'Golden Delicious'

| Characteristic | 'Y103' | 'Golden Delicious' |
|---|---|---|
| Harvest time | 10 to 15 days before 'Golden Delicious' | Mid to late September |

TABLE 1-continued

Comparison of 'Y103' to 'Golden Delicious'

| Characteristic | 'Y103' | 'Golden Delicious' |
|---|---|---|
| Flesh Color | Dark pink red and white | White |
| Surface texture | More ribbing | Less ribbing |
| Lenticels | Very prominent | Less prominent |
| Flavor | More aromatic | Less aromatic |

TABLE 2

Comparison of 'Y103' to 'SJ109'

| Characteristic | 'Y103' | 'SJ109' |
|---|---|---|
| Skin overcolor | Brown orange | Yellow green |
| Surface texture | More ribbing | Less ribbing |
| Storageability | Moderate | Short |
| Taste | Balanced sugar/acid | Acidic |
| Productivity | More productive | Less productive |

TABLE 3

Comparison of 'Y103' to 'Y101'

| Characteristic | 'Y103' | 'Y101' |
|---|---|---|
| Skin overcolor | Brown orange | Orange skin |
| Productivity | More productive | Less productive |
| Flowering | Just before 'Y101' | Just after 'Y103' |
| Aroma | More aromatic | Less aromatic |

BRIEF DESCRIPTION OF THE PHOTOGRAPHS

The accompanying photographs of the 'Y103' variety were taken in 2016, 2017 and 2018 at Seiches sur le Loir, France. The trees shown were planted in 2012.

DETAILED BOTANICAL DESCRIPTION OF THE VARIETY

Figure 1:
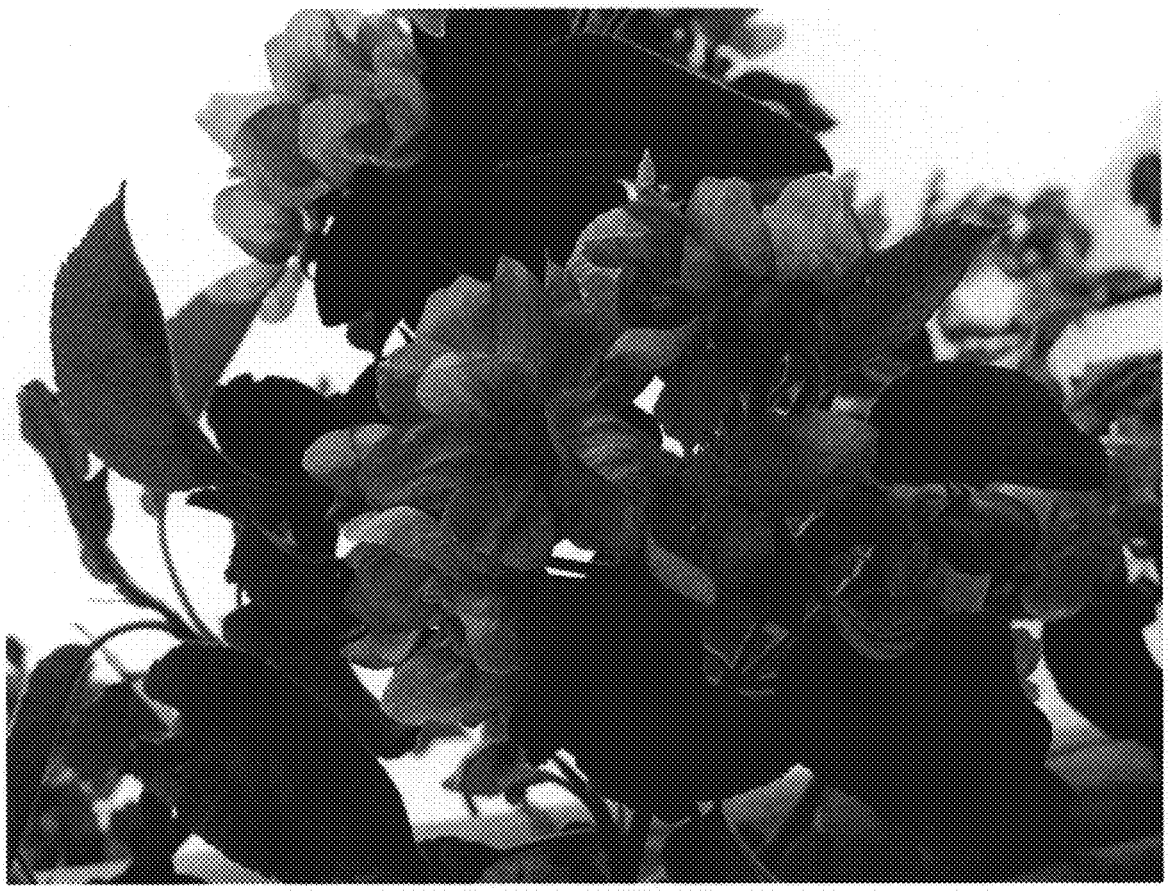
FIG. 1 shows the blossoms of a 'Y103' apple tree.
Figure 2:
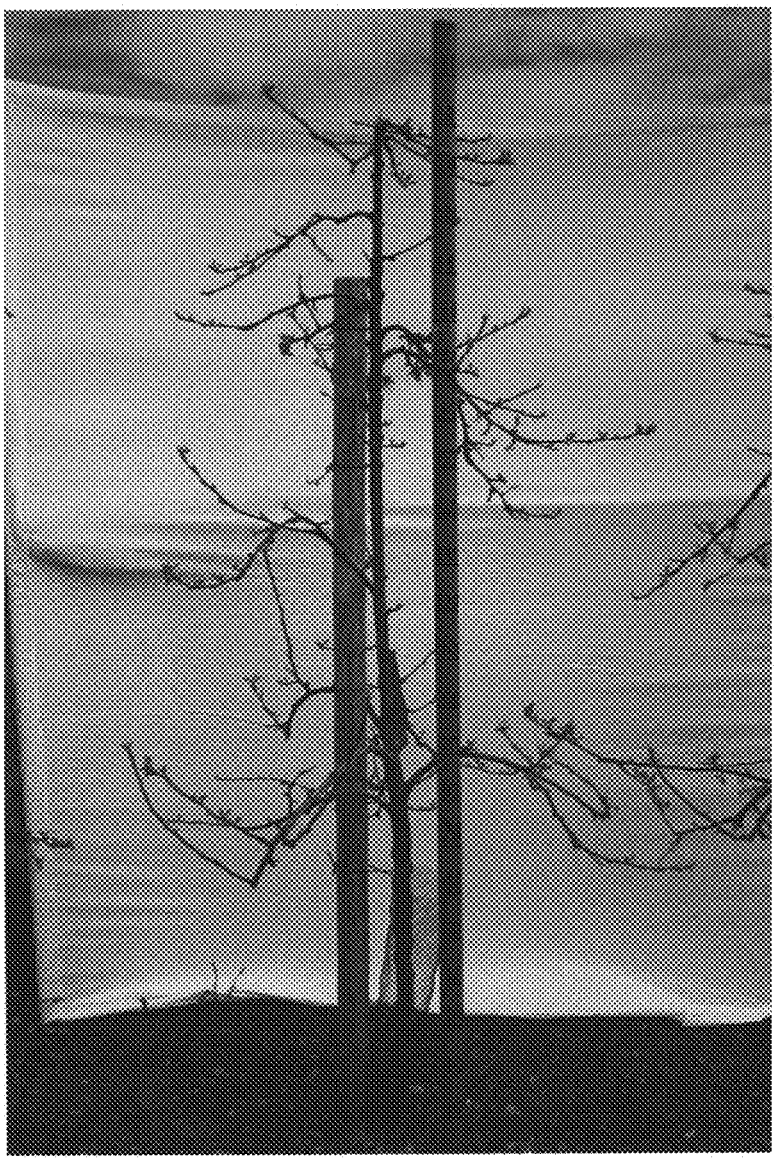
FIG. 2 shows a 'Y103' apple tree during winter.
Figure 3:
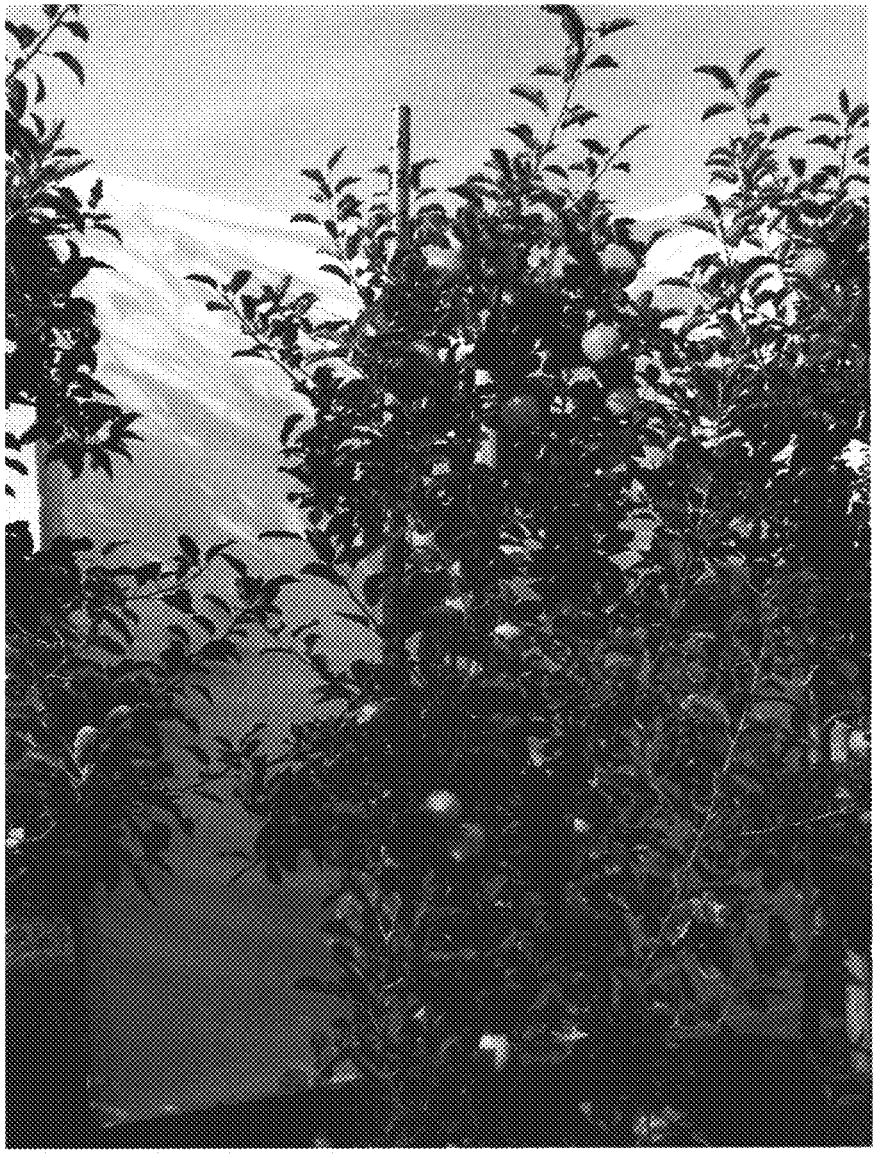
FIG. 3 shows a 'Y103' apple tree just prior to harvest.
Figure 4:
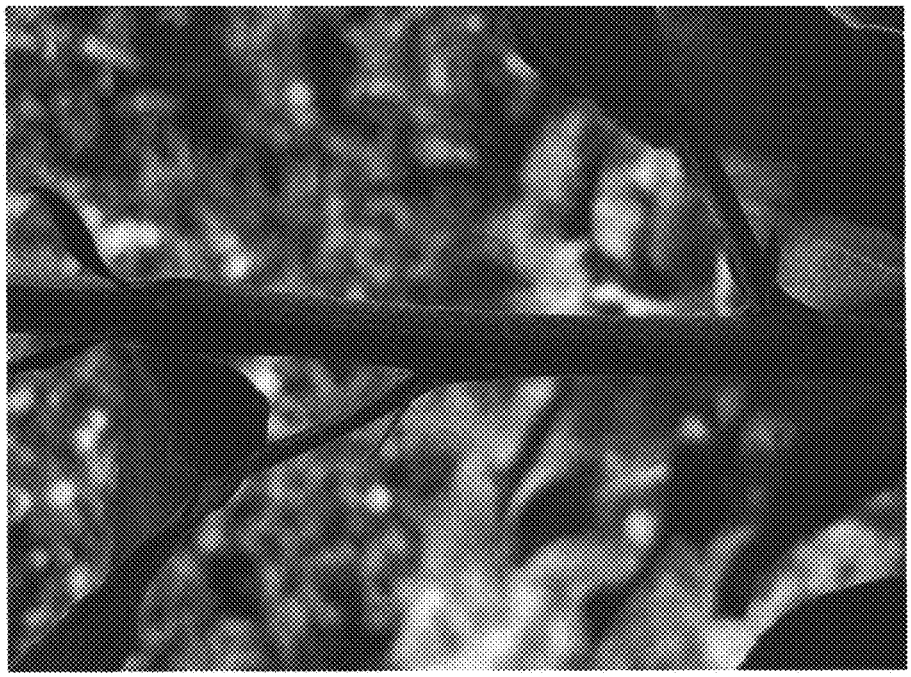
FIG. 4 shows a one-year-old shoot of a 'Y103' apple tree.
Figure 5:
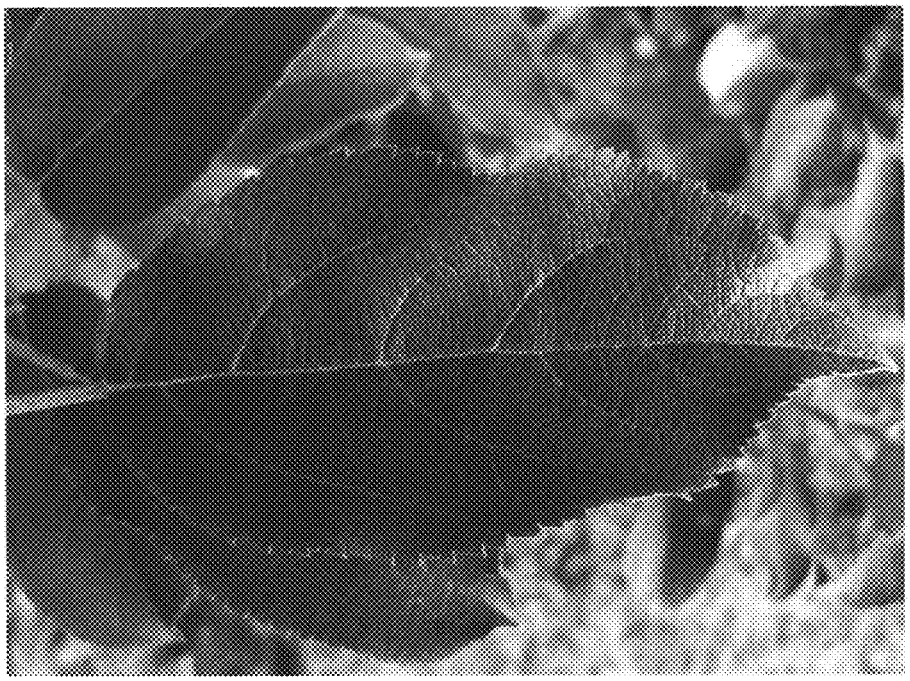
FIG. 5 shows a leaf of a 'Y103' apple tree.
Figure 6:
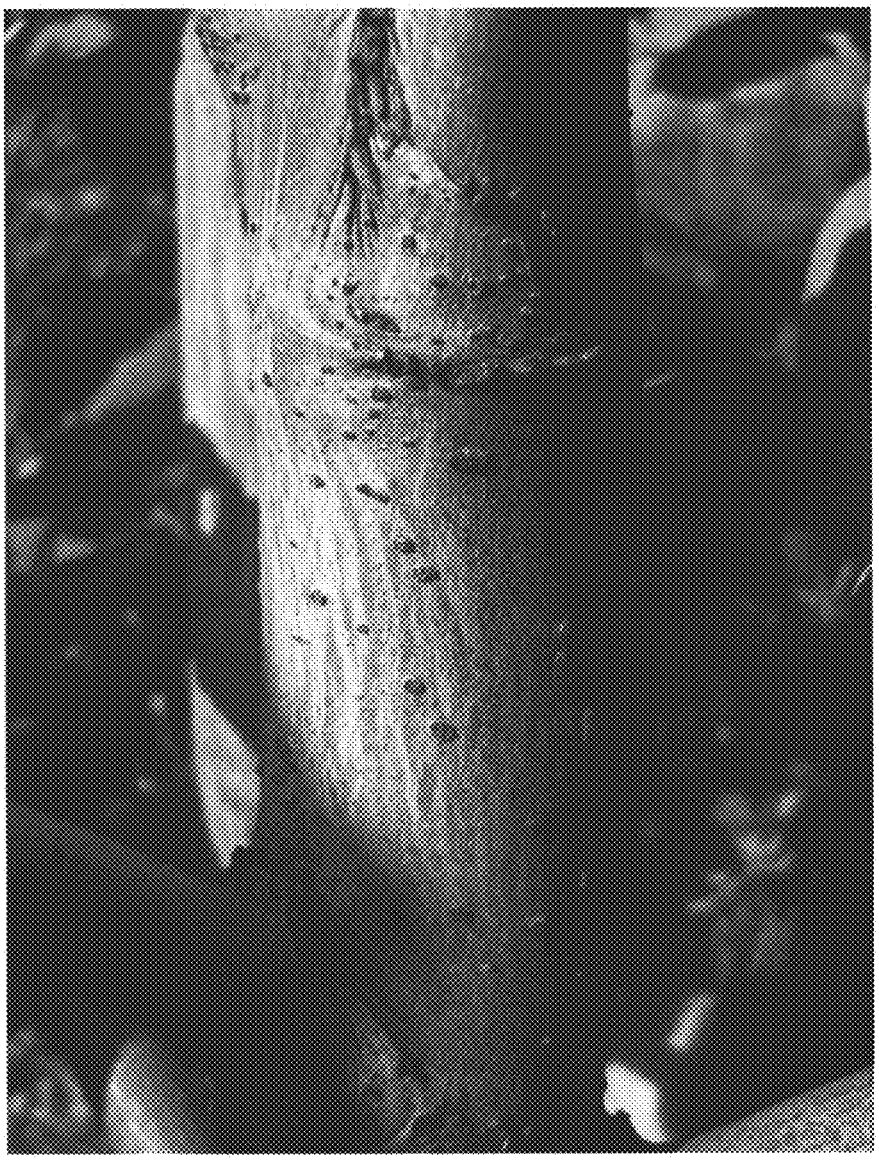
FIG. 6 shows the trunk of a 'Y103' apple tree.
Figure 7:
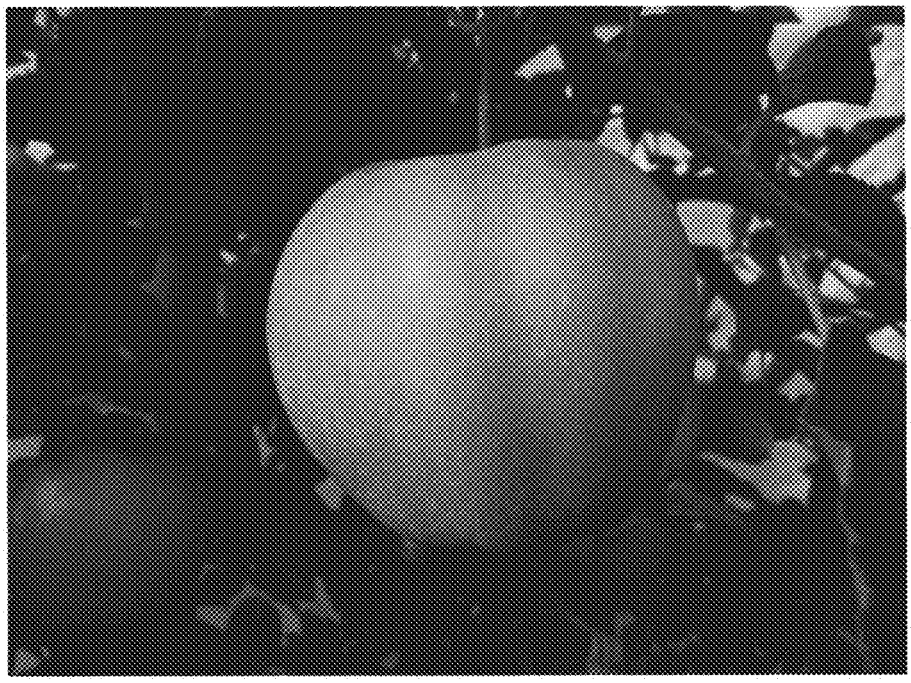
FIG. 7 shows a whole fruit of the 'Y103' apple variety.
Figure 8:
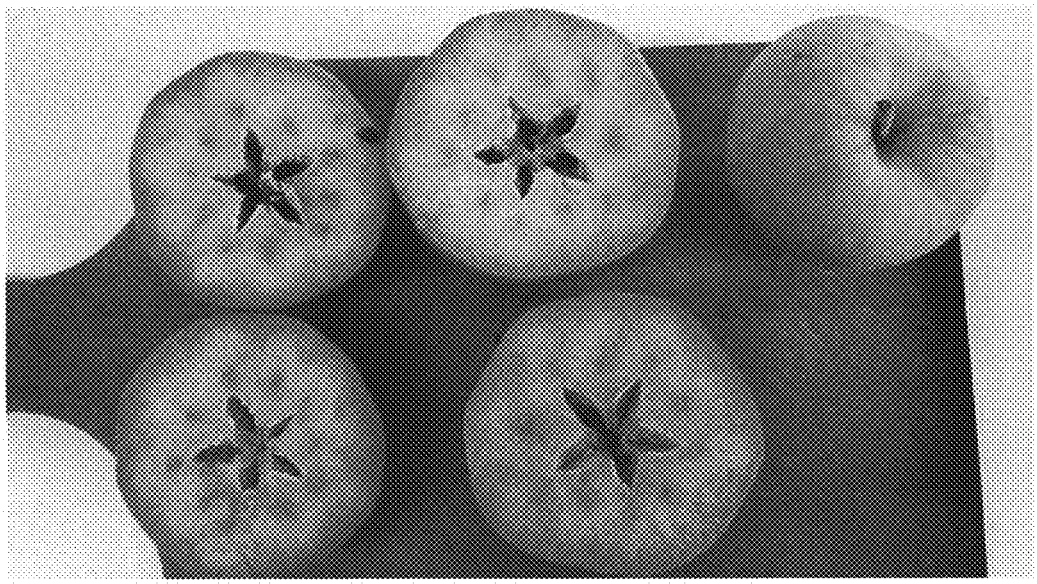
FIG. 8 shows whole and sectioned fruit of the 'Y103' apple variety.

The following detailed botanical description is based on observations made at Seiches sur le Loir, France during the 2016, 2017 and 2018 growing seasons, of trees on Pajam®2 'Cepiland' rootstock (U.S. Plant Pat. No. 7,715), planted in 2012. All colors are described according to The Royal Horticultural Society Mini Colour Chart (2005). It should be understood that the characteristics described will vary somewhat depending upon cultural practices and climatic conditions and will vary with location and season. Quantified measurements are expressed as an average of measurements taken from a number of individual plants of the new variety. The measurements of any individual plant or any group of plants of the new variety may vary from the stated average.

Tree:

*Vigor*.—Medium to high.
*Type*.—Ramified.
*Bearing*.—On shoots.
*Habit*.—Spreading to drooping.
*Spread of mature tree*.—Approximately 1.7 m.
*Height*.—Approximately 2.3 m.
*Trunk diameter* (*at* 30 *cm above the graft*).—40 mm.
*Bark texture*.—Smooth.
*Bark color*.—Grey N200C.
*Lenticel length*.—2 mm.
*Lenticel width*.—1 mm.
*Lenticel height*.—0.5 mm.
*Lenticel shape*.—Round to oblong.
*Lenticel color*.—Orange brown N170A.
*Number of lenticels per cm*$^2$.—3.

Branch (fruiting branches located at around 1 m above the graft union):

*Length*.—80 cm.
*Diameter*.—16 mm.
*Crotch angle*.—90°.
*Bark color*.—Grey N200C.
*Lenticel length*.—1.3 mm.
*Lenticel width*.—1.3 mm.
*Lenticel height*.—0.4 mm.
*Lenticel shape*.—Round.
*Lenticel color*.—Orange brown 170A.
*Number of lenticels per cm*$^2$.—3.

One year old shoot:

*Length*.—30 cm.
*Color*.—Black group 187A.
*Pubescence*.—Medium to high.
*Diameter*.—6 mm to 7 mm.
*Internode length*.—29 mm.
*Lenticel length*.—1 mm.
*Lenticel width*.—0.6 mm.
*Lenticel height*.—0.3 mm.
*Lenticel shape*.—Round to oblong.
*Number of lenticels per cm*$^2$.—7.

Flower buds:

*Quantity per spur*.—1 to 3.
*Bud shape*.—Conical.
*Apex shape*.—Rounded.
*Length*.—11 mm.
*Diameter*.—12 mm.
*Color*.—Purple red 58B.

Flowers:

*Diameter of fully open flower*.—41 mm.
*Flower depth*.—10.3 mm.
*Relative position of petal margin*.—Not touching.
*Number per cluster*.—5 to 7.
*Fragrance*.—Strong.
*Date of first bloom*.—Apr. 18, 2018 in Loire Valley, France (same as 'Golden Delicious').
*Date of full bloom*.—Apr. 19, 2018 in Loire Valley, France (4 days before 'Golden Delicious').
*Pollination requirement*.—Pollenizer required, such as 'Granny Smith' (not patented).

Petals:

*Number per flower*.—5.
*Shape*.—Elliptical.
*Length*.—21 mm.
*Width*.—15 mm.
*Apex*.—Obtuse.
*Base*.—Acute.
*Margin*.—Smooth.
*Color of upper surface*.—Pink Violet 75C.
*Color of lower surface*.—Pink Violet 67A.
*Texture of upper and lower surfaces*.—Smooth to rugulose.

Pistils:

*Quantity*.—5.
*Length*.—12 mm.
*Color*.—Light yellow green 150B.

Stigma:

*Size*.—1 mm.
*Color*.—Yellow green 145A.

Style:

*Size*.—6 mm.
*Color*.—Yellow green 145C.

Ovary:

*Length*.—4 mm.
*Width*.—2.3 mm.
*Color*.—Yellow green 145C.

Anthers:

*Quantity*.—16 to 20.
*Length*.—2.2 mm.
*Width*.—1.3 mm.
*Color*.—Light yellow brown 160B.
*Presence of pollen*.—Present.
*Pollen quantity*.—Moderate.
*Color of pollen*.—Light yellow 8C.

Pedicel:

*Length*.—30 mm.
*Diameter*.—1.5 mm.
*Color*.—Light green 138D.

Sepals:
*Quantity.*—5.
*Color.*—Upper surface — Light green 141D.
*Color.*—Lower surface — Light green 138D.
*Length.*—10.5 mm.
*Width.*—3.6 mm.
*Shape.*—Acute.
*Apex.*—Pointed.
*Margin.*—Smooth.

Leaves:
*Shape.*—Elliptical.
*Length.*—85 mm.
*Width.*—47 mm.
*Length/width ratio.*—1.8.
*Blade margin.*—Biserrate.
*Apex.*—Acute to right-angled.
*Base.*—Obtuse.
*Color.*—Upper surface — Dark green 136 A.
*Color.*—Lower surface — Green 137C.
*Texture of upper surface.*—Glabrous.
*Texture of lower surface.*—Smooth to puberulent.
*Attitude in relation to shoot.*—Upwards.

Petiole:
*Length.*—27 mm.
*Diameter.*—1.7 mm.
*Color.*—Yellow green 145C and purple 58A.

Fruit:
*Quantity per cluster.*—2 to 3.
*Diameter.*—84 mm.
*Height.*—91 mm.
*Weight.*—260 g.
*Ratio of height to width.*—1.08.
*General shape in profile.*—Conical.
*Position of maximum diameter.*—Middle of the fruit.
*Ribbing.*—Strong.
*Crowning at calyx end.*—Strong.
*Size of eye.*—Medium.
*Aperture of eye.*—Absent or weak.
*Length of sepal.*—11 mm.
*Bloom of skin.*—Weak.
*Greasiness of skin.*—Weak to moderate.
*Background color of skin.*—Yellow 7D.
*Over color of skin.*—Brown orange 34D.
*Amount of over color.*—Moderate.
*Intensity of over color.*—Light.
*Pattern of over color.*—Flushed and mottled.
*Amount of russet around stalk cavity.*—Absent to weak.
*Amount of russet on cheeks.*—Absent.
*Area of russet around eye basin.*—Absent to weak.
*Length of stalk.*—33 mm.
*Thickness of stalk.*—2.6 mm.
*Depth of stalk cavity.*—20 mm.
*Width of stalk cavity.*—32 mm.
*Depth of eye basin.*—6 mm.
*Width of eye basin.*—25 mm.
*Firmness of flesh.*—Low to medium.
*Flesh texture.*—Fine to intermediate.
*Aroma.*—Medium.
*Juiciness.*—Medium to high.
*Brix.*—13° Brix.
*Flesh color.*—Dark pink red 50B and white N155D.
*Stem color.*—Brown 199A.

Seeds:
*Quantity per fruit.*—8.
*Shape.*—Oval oblong.
*Length.*—7 mm.
*Color.*—Dark brown 165A and orange brown N170A.

Harvest:
*Time for harvest.*—Aug. 23, 2017 in Loire Valley, France (1 day before 'Galaxy' (U.S. Plant Pat. No. 6,955)).
*Number of picks.*—2.
*Harvest yield.*—Between 12 and 15 kg per tree ($6^{th}$ leaf).
*Eating quality.*—Very good.
*Disease/pest resistance/susceptibility.*—None noted.
*Storage characteristics.*—Moderate storageability at 3 to 4° C.

Market use: Fresh eating.

The invention claimed is:

1. A new and distinct apple tree substantially as described and illustrated herein.

* * * * *